United States Patent [19]

Nakamura et al.

[11] Patent Number: 4,675,276
[45] Date of Patent: Jun. 23, 1987

[54] SILVER HALIDE PHOTOGRAPHIC MATERIAL

[75] Inventors: Koki Nakamura; Tetsuro Kojima; Takashi Toyoda; Hideo Ikeda, all of Kanagawa, Japan

[73] Assignee: Fuji Photo Film Co., Ltd., Kanagawa, Japan

[21] Appl. No.: 906,710

[22] Filed: Sep. 12, 1986

Related U.S. Application Data

[63] Continuation-in-part of Ser. No. 662,112, Oct. 18, 1984, abandoned.

[30] Foreign Application Priority Data

Oct. 20, 1983 [JP] Japan ............................... 58-196560

[51] Int. Cl.⁴ ........................... G03C 1/34; G03C 5/26
[52] U.S. Cl. .................................... 430/446; 430/614; 430/510
[58] Field of Search ................ 430/614, 611, 446, 510

[56] References Cited

U.S. PATENT DOCUMENTS 4,003,910  1/1977  Bartels-Keith et al. ........ 260/308 D
4,378,424  3/1983  Altland et al. ...................... 430/552
4,459,351  7/1984  Adin et al. .......................... 430/955

*Primary Examiner*—Won H. Louie
*Attorney, Agent, or Firm*—Sughrue, Mion, Zinn, Macpeak, and Seas

[57] ABSTRACT

A silver halide photographic material containing a mesoionic 1,2,4-triazolium-3-thiolate compound in at least one hydrophilic colloidal layer of the silver halide photographic material gives photographic images having stable and excellent quality without being accompanied by the increased formation of fog and increased changes of sensitivity and gradation upon high temperature processing.

20 Claims, No Drawings

SILVER HALIDE PHOTOGRAPHIC MATERIAL

This is a continuation-in-part of application Ser. No. 662,112, filed Oct. 18, 1984, abandoned.

FIELD OF THE INVENTION

This invention relates to a silver halide photographic material and, more particularly, to a silver halide photographic material which can prevent the formation of fog occurring upon high temperature quick processing, effectively control the development speed, and provide a high-quality image.

By the term "effectively control the development speed" is meant that the reliance of a photographic material upon the conditions of the development process is reduced. Practically speaking, one of the meanings is to reduce the difference of sensitivity obtained at various temperatures of high temperature processing. In other words, it means to reduce the reliance of sensitivity on the temperature of the development process. Another meaning is to reduce as low as possible the influence of highly concentrated halogen ions (in particular, bromide ion) accumulated in a developer during development on the photographic sensitivity. That is, it means to reduce the reliance of sensitivity on halogen ions.

BACKGROUND OF THE INVENTION

Recently, for reducing the processing time for silver halide photographic materials, a process of increasing the development speed by high temperature processing has been employed. "High temperature processing" generally means processing at a temperature higher than 30° C., and the various problems of such a process are well known. In one of the problems, the increase of the development speed causes the increase of the formation of fog, the increase of the change in sensitivity and gradation, and the reduction of graininess and sharpness of images. In another one of the problems, the sensitivity and gradation largely change by the highly concentrated halogen ions (in particular, bromide ions) released and accumulated in a developer during development process, whereby a stable photographic property can not be obtained.

Various methods for overcoming these difficulties are known, but they are insufficient for eliminating these problems. For example, it is known to incorporate in a photographic material nitron as described in Japanese Patent Publication No. 28691/77 (corresponding to U.S. Pat. No. 3,915,710 and German Patent (OLS) No. 2,431,092) or an antifoggant such as 1-phenyl-5mercaptotetrazole, 5-nitrobenzotriazole, etc. However, nitron may have an antifogging action and a development restraining action but is very insufficient in the point of improving these actions and reducing reliance on the conditions of development. Also, the foregoing antifoggants have a high antifogging action, but the use of such an antifoggant greatly reduces sensitivity and does not improve the halogen reliance in developers.

Thus, silver halide photographic materials which can sufficiently endure severe development conditions required at present have not yet been obtained.

SUMMARY OF THE INVENTION

The first object of this invention is, therefore, to provide a silver halide photographic material which can be processed by high temperature quick processing required at present without being accompanied by the formation of fog, and the extremely increased change in sensitivity and gradation.

The second object of this invention is to provide a silver halide photographic material which shows less change in sensitivity and gradation by the deviation of temperature in high temperature processing.

The third object of this invention is to provide a silver halide photographic material which shows less change in sensitivity and gradation by halogen ions (in particular, bromide ions) accumulated in developer with the increase of the number of processed photographic materials.

The fourth object of this invention is to provide a silver halide photographic material which always gives excellent images by high temperature quick processing.

As the result of various investigations, the inventors have discovered that the above-described objects of this invention can be attained by incorporating at least one mesoionic 1,2,4-triazolium-3-thiolate compound to a hydrophilic colloid layer of a silver halide photographic material.

It has been confirmed that the photographic material of this invention provides images having high quality by high temperature processing and shows less reliance upon conditions of processing at high temperature as well as shows the increase of sensitivity and gradation even in low temperature processing (generally development of 2 to 20 minutes at about 20° C.).

DETAILED DESCRIPTION OF THE INVENTION

Now, as the mesoionic 1,2,4-triazolium-3-thiolate compounds which are used in this invention, the compounds shown by general formula (I) are preferred.

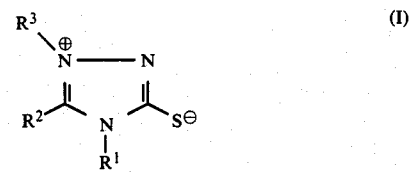

wherein $R^1$ represents a hydroxy group, a substituted (with a group such as an alkoxy group having from 1 to 7 carbon atoms, a thioalkoxy group having from 1 to 7 carbon atoms, an alkoxycarbonyl group having from 2 to 7 carbon atoms, an alkoxycarbonylalkyl group having from 3 to 7 carbon atoms, a cyano group, a carboxy group, a hydroxy group, an amino group, and a sulfamoyl group) or unsubstituted alkyl group having from 1 to 30 (preferably from 1 to 10) carbon atoms, (e.g., a methyl group, an ethyl group, a lauryl group; a 2-methoxyethyl group, an ethoxycarbonylmethyl group, etc.), a substituted (with a group such as for the above-described alkyl group) or unsubstituted alkenyl group having from 3 to 30 (preferably from 3 to 10) carbon atoms (e.g., an allyl group, a 2-butene-1-yl group, etc.), a substituted (with a group such as for the above-described alkyl group) or unsubstituted cycloalkyl group having from 3 to 30 (preferably from 3 to 10) carbon atoms (e.g., a cyclopentyl group, a cyclohexyl group, etc.), a substituted (with a group such as for the above-described alkyl group and halogen atoms, e.g., Cl, and acylamide group having from 2 to 24 carbon atoms) or unsubstituted aryl group having from 6 to 30 (preferably from 6 to 16) carbon atoms (e.g., a phenyl group, a 4-methoxyphenyl group, a 3,4-dichlorophenyl group, a 4-sulfamoylphenyl group, a 4-lauroylamidophenyl group, etc.), a substituted (with a group such as for the above-described aryl group) or unsubstituted heterocyclic ring (containing a hetero atom such as C, N, O and S) having from 1 to 30 (preferably from 1 to 16) carbon atoms (e.g., a 2-pyridyl group, a 1-octylpiperidine-4-yl group, etc.), —$NR^4R^5$ wherein $R^4$ and $R^5$ each represents a hydrogen atom, a substituted (with a group such as for the above-described alkyl group represented by $R^1$) or unsubstituted alkyl group having from 1 to 30 (preferably from 1 to 10) carbon atoms (e.g., a methyl group, an ethyl group, an ethoxycarbonyl 1 unsubstituted acyl ['

) or group having from 2 to 30 (preferably from 2 to 10) carbon atoms (e.g., an acetyl group, an octanoyl group, etc.), or a substituted (with a group such as for the above-described aryl group represented by R1) or unsubstituted aryl group having from 6 to 30 (preferably from 6 to 16) carbon atoms (e.g., a phenyl group and a 4-chlorophenyl group, etc.), said $R^4$ and $R^5$ may combine with each other to form a ring], a substituted (with a group such as for the above-described alkyl group represented by R1) or unsubstituted acyloxy group having from 2 to 30 (preferably from 2 to 10) carbon atoms (e.g., an acetoxy group, a benzoyloxy group, etc.), or a substituted (with a group such as for the above-described alkyl group represented by R1) or unsubstituted alkoxy group having from 1 to 30 (preferably from 1 to 10) carbon atoms (e.g., a methoxy group, a 2-methoxyethoxy group, etc.);

$R^2$ represents a hydrogen atom, a substituted (with a group such as for the above-described alkyl group represented by R1) or unsubstituted alkyl group having from 1 to 30 (preferably from 1 to 10) carbon atoms (e.g., a methyl group, an isobutyl group, a tert-butyl group, a methylthiomethyl group, etc.), a substituted (with a group such as for the above-described alkyl group represented by R1) or unsubstituted cycloalkyl group having from 3 to 30 (preferably from 3 to 10) carbon atoms (e.g., a cyclopentyl group, a cyclohexyl group, etc.), a substituted (with a group such as for the above-described aryl group represented by R1) or unsubstituted aryl group having from 6 to 30 (preferably from 6 to 16) carbon atoms (e.g., a phenyl group, a 4-methoxyphenyl group, a 4-chlorophenyl group, etc.), or a substituted (with a group such as for the above-described aryl group represented by R1) or unsubstituted heterocyclic ring (containing a hetero atom such as N, 0 and S) having from 1 to 30 (preferably from 1 to 16) carbon atoms (e.g., a 2-pyridyl group, a 2-furyl group, etc.); and $R^3$ represents a substituted (with a group such as for the above-described alkyl group represented by R1) or unsubstituted alkyl group having from 1 to 30 (preferably from 1 to 10) carbon atoms (e.g., a methyl group, an ethyl group, an octyl group, an octadecyl group, a methoxyethyl group, etc.), a substituted (with a group such as for the above-described alkyl group represented by R1) or unsubstituted alkenyl group having from 1 to 30 (preferably from 1 to 10) carbon atoms (e.g., an allyl group, a 2-butene-1-yl group, etc.), a substituted (with a group such as for the above-described alkyl group represented by R1) or unsubstituted cycloalkyl group having from 3 to 30 (preferably from 3 to 10) carbon atoms (e.g., a cyclopentyl group, a cyclohexyl group, etc.), a substituted (with a group such as for the above-described aryl group represented by R1) or unsubstituted aryl group having from 6 to 30 (preferably from 6 to 16) carbon atoms (e.g., a phenyl group, a 4-ethoxycarbonylphenyl group, a 3-sulfamoylphenyl group, a 4-methoxyphenyl group, etc.), or a substituted (with a group such as for the above-described aryl group represented by R1) or unsubstituted heterocyclic ring having from 1 to 30 (preferably from 1 to 16) carbon atoms and a hetero atom such as N, 0 and S (e.g., a 4-pyridyl group, a 2-piperidyl group, etc.); said R1 and R2 and said R2 and R3 may further combine with each other to form a 5-, 6- or 7-membered heterocyclic ring.

One particular embodiment of the present invention is directed to compounds of the general formula (I) wherein (i):

(1) when $R^1$ represents the hydroxy group, the heterocyclic ring, the —$NR^4R^5$ wherein $R^4$ and $R^5$ represent the acyl group or combine with each other to form the ring, the acyloxy group or the alkoxy group, $R^2$ and $R^3$ each represents a group described above;

(2) when $R^2$ represents the hydrogen aton, the cycloalkyl group or the heterocyclic group, $R^1$ and $R^3$ each represents a group as described in above; (3) when $R^3$ represents the alkenyl group or the heterocyclic ring, $R^1$ and $R^2$ represent one of the groups described above; or (ii) $R^1$ and $R^2$ or $R^2$ and $R^3$ combine with each other to form the 5-, 6- or 7-membered heterocyclic ring.

Another embodiment of the present invention is directed to compounds of the general formula (I) wherein $R^1$ represents the hydroxy group, the heterocyclic ring, the —$NR^4R^5$ (wherein $R^4$ and $R^5$ represents the acyl group or $R^4$ and $R^5$ combine with each other to form the ring), the acyloxy group, the alkoxy group, $R^2$ represents the hydrogen atom, the cycloalkyl group, the heterocyclic ring, $R^3$ represents the alkenyl group, the heterocyclic ring, or $R^1$ and $R^2$, or $R^2$ and $R^3$ combine width each other to form the 5-, 6- or 7-membered heterocyclic ring.

Then, specific examples of the mesoionic 1,2,4-triazolium-3-thiolate compounds which are used is not limited to these compounds.

Compound Example

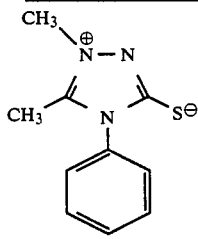

1

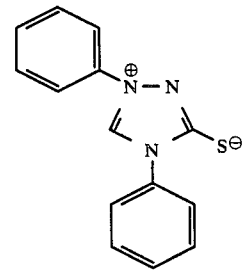

2

-continued
Compound Example
3
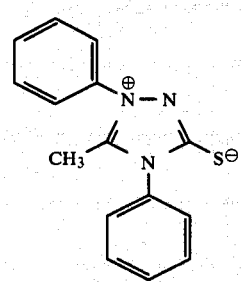
4
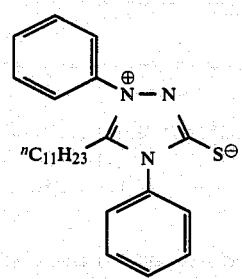
5
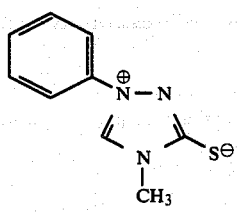
6
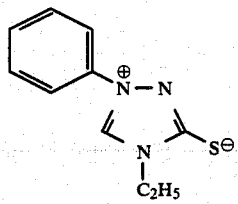
7
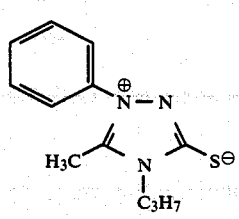
8
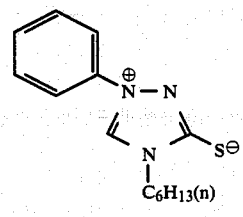
-continued
Compound Example
9
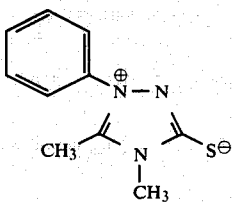
10
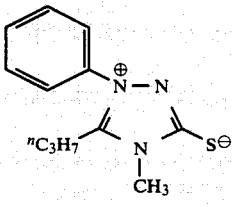
11
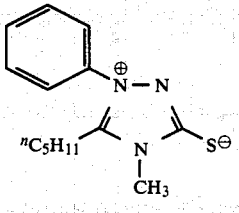
12
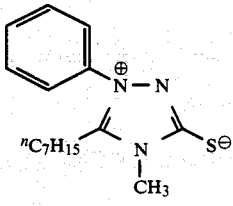
13
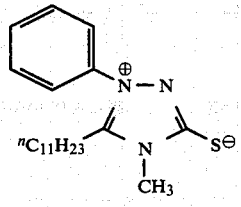
14
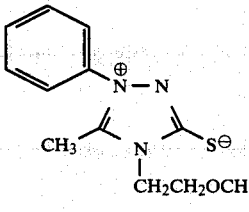
15

-continued
Compound Example
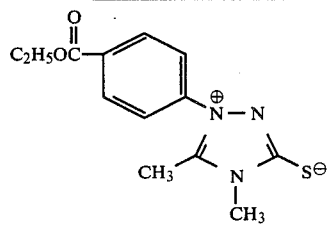 16
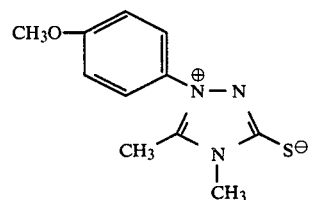 17
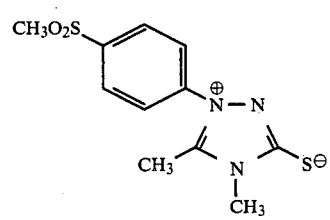 18
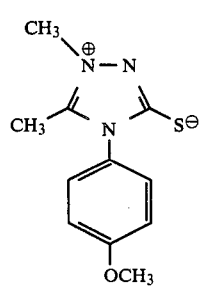 19
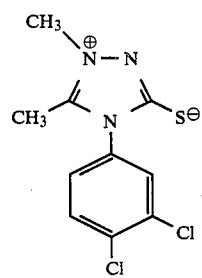 20
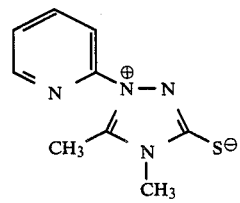 21
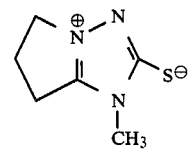 22
-continued
Compound Example
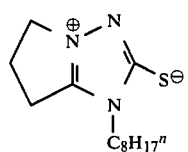 23
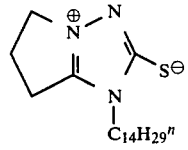 24
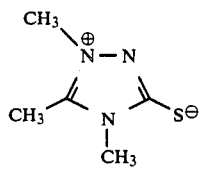 25
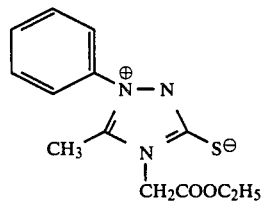 26
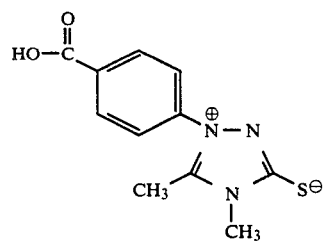 27
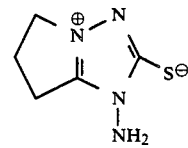 28
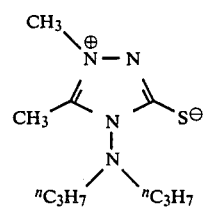 29
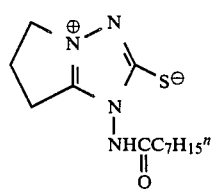 30

-continued
Compound Example

31 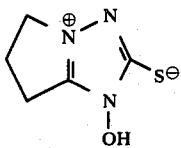

32 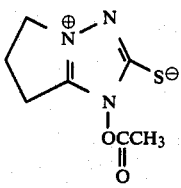

33 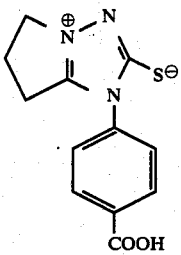

34 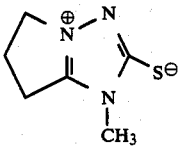

35 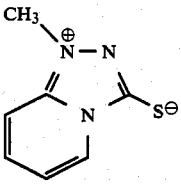

36 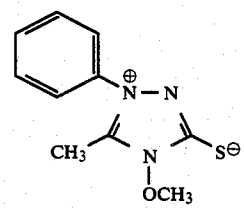

37 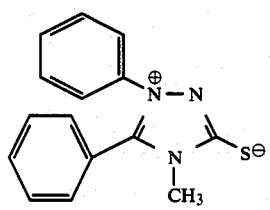

-continued
Compound Example

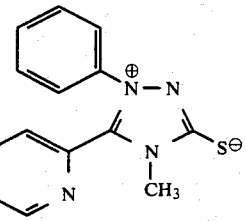 (38)

The above-described mesoionic 1,2,4-triazolium-3-thiolate compounds for use in this invention, can be generally prepared by (i) the anhydro-acylation of 1,4-di-substituted thiosemicarbazide, (ii) heating 4-acyl-1,4-di-substituted thiosemicarbazide, (iii) the reaction of N-aminoamidine and thiophosgene, (iv) the reaction of N-aminoamidine or N-thioacylhydrazine and isothiocyanic acid, (v) the reaction of N-aminoamidine or N-thioacylhydrazine and carbon disulfide-dicyclohexylcarbodiimide, or (vi) the reaction of mesoionic 1,3,4-thiadiazole or a corresponding methiodide and a primary amine More practically, the above-described compounds which are used in this invention can be prepared by the methods described in (or the methods described in the literatures cited in), for example, W. Baker and W.D. Ollis, *Chem. Ind.*, 910 (1955) (London); M. Ohta and H. Kato, *Nonbenzenoid Aromatics* (J.P. Snyder, ed.); K.P. Potts, S.K. Roy and D.P. Jones, *J. Heterocycl. Chem.*, 2, 105 (1965); K.T. Potts, S.K. Roy and D.P. Jones, *J. Org. Chem.*, 32, 2245 (1967); G.F. Duffin, J.D. Kendall and H.R.J. Waddington, *J. Chem. Soc.*, 3799 (1959); R.L. Hinmann and D. Fulton, *J. Amer. Chem. Soc.*, 80, 1895 (1958); W.D. Ollis and C.A. Ramsden, *Chem. Commun.*, 1222 (1971); W.D. Ollis and C.A. Ramsden, *J. Chem. Soc., Perkin. Trans. I*, 633 (1974); and R. Grayshey, M. Baumann and R. Hamprecht, *Tetrahedron Lett.*, 2939 (1972).

The mesoionic 1,2,4-triazolium-3-thiolate compounds which are used in this invention can be prepared according to the aforesaid methods but for explaining these methods more practically, the synthesis examples of the specific compounds are shown below.

SYNTHESIS EXAMPLE 1

Synthesis of Compound 1

By reacting 27 g of phenyl isothiocyanate and 15 g of acetylhydrazine in ethanol at room temperature, 1-acetyl-4-phenylthiosemicarbazide was formed, which was collected by filtration and refluxed in ethanol in the presence of sodium ethylate to provide 3-mercapto-5-methyl-4-phenyl-1,2,4-triazole.

In 200 ml of methanol was suspended 19.1 g of 3-mercapto-5-methyl-4-phenyl-1,2,4-triazole and then 20 g of a 28% sodium methylate solution to the suspension. After 10 minutes, 15 g of methyl iodide was added dropwise to the mixture. After performing the reaction for 10 minutes, methanol was distilled off and the product was extracted with ethyl acetate to provide 5-methyl-3-methylthio-4-phenyl-1,2,4-triazole.

Then, 10 g of 5 methyl-3-methylthio-4-phenyl-1,2,4-triazole thus obtained was mixed with 40 g of methyl iodide and the mixture was heat-refluxed for 4 hours to precipitate crystals, which were collected by filtration and recrystallized from ethanol to provide 1,5-dimethyl-3-methylthio-4-phenyl-1,2,4-triazolium iodide.

The melting point was 212 to 214° C. and the yield was 70%.

In 50 ml of pyridine was suspended 10 g of the compound thus obtained and the suspension was heat-refluxed for 30 hours. Then, pyridine was distilled off under reduced pressure from the reaction mixture and ethanol was added to the residue, whereby crystals Compound 1 by the nuclear magnetic resonance spectra, the infrared spectra, and the mass spectra.

The amount of the product thus obtained was 2.1 g, the yield was 35.6%, and the melting point was 229 to 230° C.

SYNTHESIS EXAMPLE 2

Synthesis of Compound 4

To 100 ml of toluene was added 12.2 g of 1,4-diphenylthiosemicarbazide followed by stirring and 13.0 g of lauroyl chloride was added to the mixture at room temperature. After performing the reaction for 30 minutes at room temperature, the reaction mixture was heat-refluxed for 8 hours. After cooling the reaction mixture, toluene was distilled off under reduced pressure and the residue thus formed was dissolved in ethanol. Then, aqueous ammonia was added to the solution to form colorless crystals, which were collected by filtration " and recrystallized from a mixture of chloroform and hexane.

The amount of the product was 8.7 g, the yield was 42.6% and the melting point was 205 to 208° C.

SYNTHESIS EXAMPLE 3

Synthesis of Compound 5

In 500 ml of benzene was dissolved 73 g of methyl isothiocyanate followed by stirring and after adding thereto 108 g of phenylhydrazine at room temperature, the mixture was heat-refluxed for 5 hours. After carbazide thus formed was collected by filtration.

The amount of the compound thus obtained was 122 g and the yield was 67.4%.

The compound, 4-methyl-1-phenylthiosemicarbazide thus obtained could be used for the subsequent reaction without being purified.

To 150 ml of formic acid was added 18.1 g of 4-methyl-1-phenylthiosemicarbazide obtained in the above process and the mixture was heat-refluxed for 20 hours. After cooling the reaction mixture and crystals thus formed were collected by filtration and recrystallized from methanol to provide mesoionic 4-methyl-1-phenyl1,2,4-triazolium-3-thiolate as light yellow crystals.

The amount of the product was 3.8 g, the yield was 20.0% and the melting point was 247 to 249° C.

SYNTHESIS EXAMPLE 4

Synthesis of Compound 9

After mixing 18.1 g of 4-methyl-1-phenylthiosemicarbazide prepared in Synthesis Example 3 with 25 ml of acetic acid at room temperature, 25 ml of acetic anhydride was added to the mixture with stirring and the resultant mixture was heat-refluxed for 8 hours, whereby crystals precipitated with the progress of the reaction. After cooling the reaction mixture, crystals thus formed were collected by filtration and recrystallized from a mixture of methanol and acetic acid to provide Compound 9 as colorless crystals.

The amount of the product was 13.2 g, the yield was 64.4% and the melting point was 290 to 292° C.

SYNTHESIS EXAMPLE 5 hesis of Compound 11

After mixing 10 g of 1-phenyl-4-methylthiosemicarbazide prepared in Synthesis Example 3 with toluene, g of hexanoyl chloride was added to the mixture at room temperature and the resultant mixture was stirred for 30 minutes and then heat-refluxed for 5 hours. Then, toluene was distilled off under reduced pressure from the reaction mixture, the residue thus formed was dissolved in ethanol, and then aqueous ammonia was added to the solution little by little, whereby Compound 11 was precipitated as the crystals. The crystals were recrystallized from isopropyl alcohol.

The amount of the product was 4.0 g, yield was 27.8% and the melting point was 137 to 139° C.

SYNTHESIS EXAMPLE 6

Synthesis of Compound 14

In benzene was dissolved 11.7 g of 2-methoxyethyl isothiocyanate with stirring and after adding thereto 11.9 g of phenylhydrazine at room temperature, the mixture was heat-refluxed. After performing the reaction for 6 hours, the reaction mixture was cooled and crystals thus formed were collected by filtration. The yield for the product was 66.7%. The product, 4-(2-methoxyethyl)-1-phenylthiosemicarbazide thus obtained could be used for the subsequent reaction without being purified.

In 15 ml of acetic acid was dissolved 10.0 g
i of 4-(2-methoxyethyl)-1-phenylthiosemicarbazide thus obtained with stirring and after adding 15 ml of acetic anhydride to the solution, the mixture was heat-refluxed for 8 hours. After the reaction was over, the reaction mixture was cooled, the solvent was distilled off and the product thus formed was separated and purified by column chromatography using silica gel and recrystallized from a mixture of isopropyl alcohol and diethyl ether.

The amount of the product was 2.1 g, the yield was 19.0% and the melting point was 108 to 109° C.

SYNTHESIS EXAMPLE 7

Synthēsis of Compound 16

In 100 ml of benzene were dissolved 9.3 g of 4-ethoxycarbonylphenylhydrazine and 3.6 g of methyl isothiocyanate and then the solution was refluxed with stirring. After heat-refluxing for 5 hours, the reaction mixture thus formed was cooled and crystals thus formed were collected by filtration to provide 1-(4-ethoxycarbonylphenyl)-4-methylthiosemicarbazide as colorless crystals. The product, 1-(4-ethoxycarbonylphenyl)-4-methylthiosemicarbazide thus obtained could be used for the subsequent reaction without being purified.

To 10 ml of acetic acid was added 6.5 g of 1-(4-ethoxycarbonylphenyl)-4-methylthiosemicarbazide thus obtained and after further adding 10 ml of acetic anhydride to the solution, the mixture was heat-refluxed. After the reaction was over, the reaction mixture thus obtained was cooled and crystals thus formed were collected by filtration and recrystallized from methanol.

The amount of the product was 1.8 g, the yield was 25.4% and the melting point was 248 to 250° C.

SYNTHESIS EXAMPLE 8

Synthesis of Compound 22

In methanol were dissolved δ-bromobutyric acid and hydrazine hydrate in an amount of five times the amount of δ-bromobutyric acid and the solution was heat-refluxed for 7 hours. Methanol was distilled off under reduced pressure, the residue was subjected to column chromatography using alumina, and the eluted fraction using a mixture of methanol and chloroform in 20:1 (by volume) as an eluent. Then, by distilling off the solvent from the eluate thus obtained, 1-amino-2-pyrrolidinone was obtained.

In toluene was dissolved 10 g of 1-amino-2-pyrrolidinone thus obtained and after adding thereto 7.3 g of methyl isothiocyanate, the mixture was heat-refluxed for 3 hours. After cooling the reaction mixture, crystals thus formed were collected by filtration and dried. The crystals were confirmed to be 1-(2-pyrrolidinone-1-yl)-3-methylthiourea by the nuclear magnetic resonance spectra and the mass spectra.

To 20 ml of acetic acid was added 14 g of 1-(2-pyrrolidinone-1-yl)-3-methylthiourea thus obtained followed by sitrring and after adding thereto 20 ml of acetic anhydride, the mixture was heat-refluxed. After the reaction was over, the solvent was distilled off and the residue thus formed was recrystallized from ethanol.

The amount of the product was 3.4 g, the yield was 27.1% and the melting point was 257° to 259° C.

The mesoionic 1,2,4-triazolium-3-thiolate compounds may also be used as a combination of two or more kinds thereof.

The foregoing compounds which are used in this invention may be incorporated in any hydrophilic colloidal layers of silver halide photographic materials, such as silver halide emulsion layers, subbing layers, protective layers, interlayers, filter layers, antihalation layers, etc., and preferably be incorporated in a silver halide layer.

For incorporating the foregoing compound in these photographic layers, the compound may be added to the coating liquid for forming the photographic layer as it is or as a solution in a solvent giving no bad influences on the photographic material, such as water, alcohol, etc., in a proper concentration. Also, the compound may be dispersed by emulsification in the aqueous solution for the photographic layer as a solution in a high boiling organic solvent or a low boiling organic solvent. Furthermore, the compound may be added to the coating liquid for the photographic layer as a polymer latex impregnated with the compound by the method described in Japanese Patent Application (OPI) Nos. 39853/76, 59942/76 and 32552/79 (the term "OPI" as used herein refers to a "published unexamined Japanese patent application"), U.S. Pat. No. 4,100,363, etc.

The compound may be added to the coating liquid for the photographic layer in any step during the production of the photographic material but it is generally preferred to incorporate the compound directly before coating the coating liquid.

The addition amount of the compound is from $1 \times 10^{-8}$ to $7 \times 10^{-3}$ mole, preferably not less than $1 \times 10^{-5}$ mole, and more preferably not less than $5 \times 10^{-5}$ mole per mole of silver in the photographic material.

The silver halide for use in this invention includes silver chloride, silver bromide, silver iodide, silver chlorobromide, silver chloroiodide, silver iodobromide, silver chloroiodobromide, etc.

These silver halide grains may be coarse grains, fine grains, or mixed grains thereof, and the silver halide grains are formed by a known method such as a single jet method, a double jet method, and a controlled double jet method.

Furthermore, the silver halide grains may have a crystal structure having a uniform property throughout the grains, a layer structure having different property between the internal portion and the external portion of the grain, or of a so-called conversion type as described in British Pat. No. 635,841 and U.S. Pat. No. 3,622,318. Also, the silver halide grains may be of a type forming a latent image mainly on the surface of the grain or of an internal latent image type forming a latent image in the internal portion of the grain. The silver halide photographic emulsion containing these silver halide grains can be prepared by various methods such as an ammonia method, a neutralization method, an acid method, etc., as described in, for example, Mees, *The Theory of Photographic Process*, published by Macmillan Co., Glafkides, *Photographic Chemistry*, published by Fountain Press Co., *Research Disclosure*, Vol 176 (December, 1978), RD-17643, etc.

The mean diameter of silver halide grains which are used in this invention is preferably from about 0.04 micron to about 4 microns (measured by, for example, a number average method using a projected area method).

During the formation of the silver halide grains, ammonia, potassium thiocyanate, ammonium thiocyanate, thioether compounds (described in, e.g., U.S. Pat. No. 3,271,157, 3,574,628, 3,704,130, 4,297,439, 4,276,374, etc.), thion compounds (described in, for example, Japanese Patent Application (OPI) Nos. 144319/78, 82408/78, 77737/80, etc.), amine compounds (described in, for example, Japanese Patent Application (OPI) No. 100717/79), etc., as a silver halide solvent for controlling the growth of the silver halide grains.

Also, during the formation of the silver halide grains or before or after the formation of the silver halide grains, a water-soluble rhodium compound and/or a water-soluble iridium compound may be added to the system.

The silver halide photographic emulsions for use in this invention can be sensitized by an ordinary chemical sensitization method, such as a gold sensitization (as described in U.S. Pat. Nos. 2,540,085, 2,597,876, 2,597,915, 2,399,083, etc.), a sensitization by the ion of a metal belonging to group VIII of the Periodic Table (described in U.S. Pat. Nos. 2,448,060, 2,540,086, 2,566,245, 2,566,263, 2,598,079, etc.), a sulfur sensitization (described in U.S. Pat. Nos. 1,574,944, 2,278,947, 2,440,206, 2,521,926, 3,021,215, 3,038,805, 2,410,689, 3,189,458, 3,415,649, 3,635,717, etc.), a reduction sensitization (described in U.S. Pat. Nos. 2,518,698, 2,419,974, 2,983,610, *Research Disclosure*, Vol. 176 (December, 1978), RD-17643, Chapter III, etc.), a sensitization by a thioether compound (described in U.S. Pat. Nos. 2,521,926, 3,021,215, 3,038,805, 3,046,129, 3,046,132, 3,046,133, 3,046,134, 3,046,135, 3,057,724, 3,062,646, 3,165,552, 3,189,458, 3,192,046, 3,506,443, 3,671,260, 3,574,709, 3,625,697, 3,635,717, 4,198,240, etc.), or a combination of these sensitization methods.

More practically, the chemical sensitizer for use in the foregoing chemical sensitization includes a sulfur sensitizer such as allyl thiocarbamide, thiourea, sodium thiosulfate, thioether, cystine, etc.; a noble metal sensitizer such as potassium chloroaurate, aurous thiosulfate, potassium chloropalladate, etc.; and a reduction sensitizer such as tin chloride, phenylhydrazine, reductone, etc.

Other examples of the sensitizers which can be also used in this invention are polyoxyethylene derivatives (described in British Pat. No. 981,470, Japanese Patent Publication No. 6475/66, British Pat. No. 2,716,062, etc.), polyoxypropylene derivatives, derivatives having a quaternary ammonium group, etc.

To the silver halide photographic emulsions for use in this invention may be added various compounds for preventing the reduction in sensitivity and the formation of fog during the production, storing, and processing of the photographic materials. As these compounds, well-known are nitrobenzimidazole, ammonium chloroplatinate, 4-hydroxy-6-methyl-1,3,3a,7-tetraazaindene, 3-methylbenzothiazole, 1-phenyl-5-mercaptotetrazole, various heterocyclic compounds, mercury-containing compounds, mercapto compounds, metal salts, etc. Other examples of the compounds which can be used for the foregoing purposes in this invention described in K. Mees, *The Theory of the Photographic Process*, 3rd Edition, 1966, from page 344 to page 349 together with the original literature cited therein include the thiazolium salts described in U.S. Pat. Nos. 2,131,038, 2,694,716, etc.; the azaindenes described in U.S. Pat. Nos. 2,886,437, 2,444,605, etc.; the urazols described in U.S. Pat. No. 3,287,135, etc.; the sulfocatechols described in U.S. Pat. No. 3,236,652, etc.; the oximes described in British Pat. No. 623,448, etc.; the mercaptotetrazoles described in U.S. Pat. Nos. 2,403,927, 3,266,897, 3,397,987, etc.; nitron; nitroindazoles; the polyvalent metal salts described in U.S. Pat. No. 2,839,405, etc.; the thiuronium salts described in U.S. Pat. No. 3,220,839, etc.; and the salts of palladium, platinum, and gold described in U.S. Pat. Nos. 2,566,263, 2,597,915, etc.

The silver halide emulsions for use in this invention can be sensitized by using spectral sensitizing dyes. Examples of such sensitizing dyes are described in, for example, U.S. Pat. Nos. 3,703,377, 2,688,545, 3,397,060, 3,615,635, 3,628,964, British Pat. Nos. 1,242,588 and 1,293,862, Japanese Patent Publication Nos. 4936/68, 14030/69 and 10773/68, U.S. Pat. No. 3,416,927, Japanese Patent Publication No. 4930/68, U.S. Pat. Nos. 3,615,613, 3,615,632, 3,617,295, 3,635,721, etc.

Also, if necessary, these sensitizing dyes may be used as a combination thereof.

The silver halide emulsions may be hardened by an ordinary method. Examples of the hardening agent which can be used for the purpose are aldehyde compounds such as formaldehyde, glutaraldehyde, etc.; ketone compounds such as diacetyl, cyclopentanedione, etc.; compounds having a reactive halogen such as bis(2-chloroethylurea), 2-hydroxy-4,6-dichloro-1,3,5-triazine, as well as those as shown in U.S. Pat. Nos. 3,288,775, 2,732,303, British Pat. Nos. 974,723, 1,167,207, etc.; compounds having a reactive olefin such as divinylsulfone, 5-acetyl-1,3-diacryloylhexahydro-1,3,5-triazine as well as those as shown in U.S. Pat. Nos. 3,635,718, 3,232,763, British Pat. No. 994,869, etc.; N-methylol compounds such as N-hydroxymethylphthalimide and those as shown in U.S. Pat. Nos. 2,732,316, 2,586,168, etc.; the isocyanates as shown in U.S. Pat. No. 3,103,437, etc.; the aziridine compounds as shown in U.S. Pat. Nos. 3,017,280, 2,983,611, etc.; the acid derivatives as shown in U.S. Pat. Nos. 2,725,294, 2,725,295, etc.; the carbodiimide series compounds as shown in U.S. Pat. No. 3,100,704, etc.; the epoxy compounds as shown in U.S. Pat. No. 3,091,537, etc.; the isooxazole compounds as shown in U.S. Pat. Nos. 3,321,313, 3,543,292, etc.; halogenocarboxyaldehydes such as mucochloric acid, etc.; dioxane derivatives such as dihydroxydioxane, dichlorodioxane, etc.; and inorganic hardening agents such as chromium alum, zirconium sulfate, etc.

Also, in place of the foregoing compounds, precursors of them, such as, for example, alkali metal bisulfitealdehyde addition products, methylol derivatives of hydantoin, primary aliphatic nitroalcohols, etc., may be used as hardening agents.

The silver halide photographic emulsions for use in this invention may contain surface active agents solely or as a mixture of them. These surface active agents are mainly used as a coating aid but are used for other purposes such as for improving the emulsifying dispersion, for improving sensitization characteristics, for antistatic prevention, for preventing adhesion of photographic materials, etc. These surface active agents include natural surface active agents such as saponin, etc.; nonionic surface active agents such as alkylene oxide series surface active agents, glycerol series surface active agents, glycidol series surface active agents, etc.; cationic surface active agents such as higher alkylamines, quaternary ammonium salts, pyridine and other heterocyclic rings, phosphonium salts, sulfonium salts, etc.; anionic surface active agents having an acid group such as a carboxylic acid group, a sulfonic acid group, a phosphoric acid group, a sulfuric acid ester group, a phosphoric acid ester group, etc.; and amphoteric surface active agents such as amino acids, aminosulfonic acids, sulfuric acid esters or phosphoric acid esters of aminoalcohol, etc.

The polyalkylene oxide compounds which can be used in this invention include the condensation products of polyalkylene oxide composed of an alkylene oxide having 2 to 4 carbon atoms, such as ethylene oxide, propylene-1,2-oxide, butylene-1,2-oxide, etc., preferably composed of at least 10 units of ethylene oxide and a compound having at least one active hydrogen, such as water, an aliphatic alcohol, an aromatic alcohol, a fatty acid, an organic amine, a hexytol derivatives, etc.; and a block copolymer of two or more kinds of polyalkylene oxides.

Specific examples of such polyalkylene oxide compounds are polyalkylene glycols, polyalkylene glycol alkyl ethers, polyalkylene glycol aryl ethers, polyalkylene glycol alkylaryl ethers, polyalkylene glycol esters, polyalkylene glycol fatty acid amides, polyalkylene glycol amines, polyalkylene glycol block copolymers, polyalkylene glycol graft polymers, etc. It is necessary that the molecular weight of the polyalkylene oxide compound for use in this invention is higher than 600.

This invention can be applied to color photographic materials. In this case, for the color reproduction, a subtractive color photographic process is usually used, and silver halide emulsions selectively sensitive to blue, green and red and yellow, magenta, and cyan color formers which are in a complementary color relationship with the aforesaid colors are used. For forming a yellow color image couplers, for example, acylacetanilide series couplers, dibenzoylmethane series couplers, etc., are used. For forming a magenta color image, pyrazolone, pyrazolobenzimidazole, cyanoacetophenone, and indazolone series couplers are mainly used. For forming a cyan color image, phenol series couplers such as phenols and naphthols are mainly used.

Specific examples of the magenta coloring couplers are described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,810,464, West German Patent Application (OLS) Nos. 2,408,665, 2,417,945, 2,418,959 and 2,424,467, Japanese Patent Publication No. 6031/65, Japanese Patent Application (OPI) Nos. 20826/76, 58922/77, 129538/74, 74027/74, 159336/75, 42121/77, 74028/74, 60233/75, 26541/76, 55122/78, etc.

Specific examples of the yellow coloring couplers are described in U.S. Pat. Nos. 2,875,057, 3,265,506, 3,408,194, 3,551,155, 3,582,322, 3,725,072 and 3,891,445, West German Pat. No. 1,547,868, West German Patent Application (OLS) Nos. 2,219,917, 2,261,361, 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77, 115219/77, etc.

Specific examples of the cyan coloring couplers are described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, West German Patent Application (OLS) Nos. 2,414,830, 2,454,329, Japanese Patent Application (OPI) Nos. 59838/73, 26034/76, 5055/73, 146828/76, 69624/77, 90932/77, etc.

The color photographic materials of this invention can further contain colored couplers described in, for example, U.S. Pat. Nos. 3,476,560, 2,521,908 and 3,034,892, Japanese Patent Publication Nos. 2016/69, 22335/63, 11304/67, 32461/69, Japanese Patent Application (OPI) Nos. 26034/76 and 42121/77, West German Patent Application (OLS) No. 2,418,959, etc.

The color photographic materials of this invention can also contain development inhibitor releasing (DIR) couplers described in, for example, U.S. Pat. Nos. 3,227,554, 3,617,291, 3,701,783, 3,790,384 and 3,632,345, West German Patent Application (OLS) Nos. 2,414,006, 2,454,301 and 2,454,329, British Pat. No. 953,454, Japanese Patent Application (OPI) Nos. 69624/77 and 122335/74, Japanese Patent Publication No. 16141/76, etc.

Other than the DIR couplers, the photographic material of this invention may contain compounds which release a development inhibitor with the progress of development. Specific examples of such compounds are described in, for example, U.S. Pat. No. 3,297,445 and 3,379,529, West German Patent Application (OLS) No. 2,417,914, Japanese Patent Application (OPI) Nos. 15271/77, 9116/78, etc.

These couplers may be incorporated in silver halide emulsions or aqueous solution of hydrophilic colloid by conventional methods. For example, the couplers can be dispersed by a method of dispersing the coupler as a mixture with a high boiling organic solvent such as dibutyl phthalate, tricresyl phosphate, wax, higher fatty acid or an ester thereof, etc., as described in, for example, U.S. Pat. Nos. 2,304,939, 2,322,027, etc.; by dispersing after mixing the coupler with a low boiling organic solvent or a water-soluble organic solvent; by dispersing after further mixing therewith a high boiling organic solvent as described in, for example, U.S. Pat. Nos. 2,801,170, 2,801,171, 2,949,360, etc.; by dispersing the coupler, when the coupler itself has a sufficiently low melting point (e.g., lower than 75° C.), alone or together with other coupler such as a colored coupler or an uncolored coupler as described in, for example, German Pat. No. 1,143,707, etc.

For dispersing the couplers, ordinary auxiliary dispersing agents may be used and as such auxiliary dispersing agents, there are anionic surface active agents (e.g., sodium alkylbenzenesulfonate, sodium dioctylsulfosuccinate, sodium dodecylsulfate, sodium alkylnaphthalenesulfonate, Fischer-type couplers, etc.), amphoteric surface active agents (e.g., N-tetradecyl-N,N-dipolyethylene α-betaine, etc.) and nonionic surface active agents (e.g., sorbitan monolaurate, etc.).

The silver halide photographic emulsions which are used in this invention may further contain a protective colloid such as gelatin; acylated gelatin such as phthalated gelatin, malonated gelatin, etc.; cellulose compounds such as hydroxyethyl cellulose, carboxymethyl cellulose, etc.; soluble starch such as dextrin, etc.; and hydrophilic polymers such as polyvinyl alcohol, polyvinylpyrrolidone, polyacrylamide, polystyrenesulfonic acid, etc.

Furthermore, the silver halide photographic emulsions may contain the polymer latexes composed of the homopolymer or copolymer of alkyl acrylate, alkyl methacrylate, acrylic acid, glycidyl acrylate, etc., for improving the dimensional stability of the photographic materials and for improving the properties of the films as disclosed in U.S. Pat. Nos. 3,411,911, 3,411,912, 3,142,568, 3,325,286 and 3,547,650 and Japanese Patent Publication No. 5331/60.

Moreover, the silver halide photographic materials of this invention may contain a developing agent such as hydroquinones, catechols, aminophenols; 3-pyrazolidones; ascorbic acid or the derivatives thereof; reductones, phenylenediamines; and a combination of these developing agents. The developing agent can be incorporated in a silver halide emulsion layer and/or other photographic layers (e.g., a protective layer, interlayers, a filter layer, an antihalation layer, a emulsion layer.

The developing agent can be added to the coating composition for the desired photographic layer as a solution in a proper solvent or as a dispersion of it as described in U.S. Pat. No. 2,592,368, French Pat. No. 1,505,778, etc.

Examples of the development accelerators which can be used in this invention are described in, for example, U.S. Pat. Nos. 3,288,612, 3,333,959, 3,345,175, 3,708,303, British Pat. No. 1,098,748, and West German Pat. Nos. 1,141,531, 1,183,784, etc.

The silver halide photographic emulsions for use in this invention may further contain antistatic agents, plasticizers, optical whitening agents, air fogging preventing agents, toning agents, etc. Specific materials of them are described in *Research Disclosure*, vol. 176 (December 1978), RD-17643.

The mesoionic 1,2,4-triazolium-3-thiolate compounds in this invention can be widely used for black-and-white photographic materials such as radiographic films (e.g., direct X-ray films, industrial X-ray films), general black-and-white photographic films, lithographic films, scanner films, black-and-white photographic papers, etc.; color photographic materials such as color negative films, color reversal films, color photographic papers, etc., as well as color photographic materials by a silver salt process or a color diffusion transfer photographic process; and color photographic materials by a silver dye bleaching process.

The exposure for obtaining a photographic image using the photographic materials of this invention may be performed by using an ordinary method. That is, various light sources such as natural light (sunlight), a tungsten lamp, a fluorescent lamp, a mercury lamp, a xenon arc lamp, a carbon arc lamp, a xenon flash lamp, flying spot cathode ray tube, light emitting diode, laser light (e.g., gas laser, YAG laser, dye laser, semiconductor laser, etc.) including infrared rays. Also, the light emitted from a phosphor excited by electron beam, X-rays, $\gamma$-rays, $\alpha$-rays. etc., may be employed as the light source.

The exposure time is usually from 1/1,000 sec to 1 sec as for camera use but may be shorter than 1/1,000 sec, for example, an exposure of $1/10^4$ to $1/10^6$ sec as the case of using a xenon flash lamp or a cathode ray tube, or may be longer than 1 sec. If necessary, the spectral composition of light used for the exposure can be controlled using color filter or filters.

There is no particular restriction about the development process of the silver halide photographic materials of this invention, and, for example, the known processes and known processing liquids described in *Research Disclosure*, Vol. 176, pages 28–30 can be employed in this invention. The photographic process may be a photographic process for forming silver images (black-and-white photographic process) or a photographic process for forming dye images (color photographic process) according to the purposes. The processing temperature is usually selected from the range of 18° C. to 50° C. but may be lower than 18° C. or over 50° C.

The present invention is especially preferable in restraining formation of fog and change of photographic characteristics upon high temperature quick processings at, for example, 30° to 50° C. of developing temperature and for 20 to 240 seconds (preferably for 20 to 150 seconds for black-and-white development and for 120 to 240 seconds for color development).

A developer which is used for a black-and-white photographic process can contain known developing agents such as dihydroxybenzenes (e.g., hydroquinone), 3-pyrazolidones (e.g., 1-phenyl-3-pyrazolidone, etc.), aminophenols (e.g., N-methyl-p-aminophenol, etc.), etc. They can be used solely or as a combination thereof. The developers may further contain preservatives, alkali agents, pH buffers, antifoggants, etc., and further, if necessary, dissolution aids, toning agents, development accelerators, surface active agents, defoaming agents, water softeners, hardening agents, tackifiers, etc.

To the silver halide photographic emulsions in this invention can be applied a so-called "lithographic type" development process. By the term "lithographic type" development process is meant a development process for infectiously performing the development step usually using dihydroxybenzene as a developing agent under a low sulfite ion concentration for the photographic reproduction of line images or the photographic reproduction of a halftone image by dot. Details are described in Mason, *Photographic Processing Chemistry*, pages 163–165 (1966).

A color image can be obtained by an ordinary process. For example, there are a nega-posi process (described in, for example, *Journal of the Society of Motion Picture and Television Engineers*, Vol. 61, 667 to 701 (1953)), a color reversal process wherein the photographic material is developed in a developer containing a black-and-white developing agent to form a negative silver image and then by performing at least one overall light exposure or other suitable fogging treatment and then performing a color development, a positive dye image is obtained; and a silver dye bleaching process wherein after imagewise exposing a silver halide emulsion layer containing a dye, the emulsion layer is developed to form a silver image and the dye in the emulsion layer is bleached with the silver image as the bleaching catalyst.

A color developer is generally composed of an alkaline aqueous solution containing a color developing agent. For the color developer, known primary aromatic amine developing agent such as phenylenediamines (e.g., 4-amino-N,N-diethylaniline, 3-methyl-4-amino-N,N-diethylaniline, 4-amino-N-ethyl-N-$\beta$-hydroxyethylaniline, -methyl-4-amino-N-ethyl-N-$\beta$-hydroxyethylaniline, 3-methyl-4-amino-N-ethyl-N-$\beta$-methanesulfonamidoethylaniline, 4-amino-3-methyl-N-ethyl-N-$\beta$-methoxyethylaniline, etc.) can be used.

Other color developing agents which can be used for developing the color photographic materials of this invention are described in L.F.A. Mason, *Photographic Processing Chemistry*, pages 226–229, published by Focal Press, 1966, U.S. Pat. Nos. 2,193,015 and 2,592,364, Japanese Patent Application (OPI) No. 64933/73, etc.

After color development the photographic material is usually bleached. The bleach process may be performed simultaneously with fix process or may be performed separately therefrom. As the bleaching agent, there are compounds of multivalent metals such as iron (III), cobalt (IV), chromium (VI), copper (II), etc., peracids, quinones, nitroso compounds, etc.

Then, the following examples are intended to illustrate this invention in more detail but not to limit in any way.

EXAMPLE 1

A silver halide emulsion was prepared as follows. An aqueous solution of silver nitrate and an aqueous solution of an alkali halide were added to an aqueous gelatin solution by an ordinary ammonia method to form silver iodobromide grains (AgI: 2 mole %) having a mean grain size of 1.0 $\mu$ and then applying thereto a gold and sulfur sensitization using chloroauric acid and sodium thiosulfate and then adding 4-hydroxy-6-methyl-1,3,3a,7-tetraazaindene to the emulsion as a stabilizer, a photosensitive silver iodobromide emulsion was prepared.

After adding each of the mesoionic 1,2,4-triazolium-3-thiolate compounds illustrated in Table 1 to each of the silver halide emulsions thus prepared, each of the resultant emulsions was coated on a film support to provide Samples 1 to 9. Each of the samples was stepwise exposed through an optical wedge using a sensitometer and after processing the sample by an Automatic Processor RU (made by Fuji Photo Film Co., Ltd.) using following Developer A and Fix Solution A for 90 seconds at a development temperature of 31° C., 35° C. and 37° C., the photographic properties were measured and the results thus obtained are shown in Table 1 below.

| Developer A | |
| --- | --- |
| Ethylenediaminetetraacetate | 1.2 g |
| Sodium Sulfite (anhydrous) | 50.0 g |
| Potassium Hydroxide | 20.0 g |
| Hydroquinone | 25.0 g |
| 1-Phenyl-3-pyrazolidone | 1.5 g |
| Boric Acid | 10.0 g |
| Triethylene Glycol | 25.0 g |
| Glutaraldehyde | 5.0 g |
| Potassium Bromide | 6.0 g |
| Glacial Acetic Acid | 3.0 g |
| Sodium Hydrogensulfite (anhydrous) | 4.5 g |
| 5-Nitroindazole | 0.15 g |
| 5-Methylbenzotriazole | 0.03 g |
| Water to make | 1 liter |

The pH of the composition was adjusted to about 10.30 at 25° C.

| Fix Solution A | |
| --- | --- |
| Ammonium Thiosulfate | 200.0 g |
| Sodium Sulfite (anhydrous) | 20.0 g |
| Boric Acid | 8.0 g |
| Ethylenediaminetetraacetic Acid | 0.1 g |
| Aluminum Sulfate | 15.0 g |
| Sulfuric Acid | 2.0 g |
| Glacial Acetic Acid | 22.0 g |
| Water to make | 1 liter |

The pH of the composition was adjusted to about 4.10 at 25° C.

compared to Samples 2 and 3 using the comparison compound and in the former samples, the increase of the sensitivity in the case of processing at 37° C. only is restrained without reducing the sensitivity in the processings at 31° C. and 35° C. too much and hence these samples have less processing temperature reliance of sensitivity.

Also, in the samples of this invention, the increase of gamma in the processing at 37° C. is effectively restrained and hence the processing temperature reliance of gamma is very low. Thus, the above results show that the mesoionic 1,2,4-triazolium-3-thiolate compounds in this invention restrain the formation of fog and the increase of sensitivity and gradation in high temperature processing and always provide stable and high quality photographic properties.

EXAMPLE 2

Each of Samples 1 to 9 as in Example 1 was exposed by the same manner as in Example 1 and subjected to the following processings using each of the, following developers.

Developer A: Same as the developer used in Example 1.

Developer B: The developer was prepared by adding 11.1 g of potassium bromide per liter of Developer A. (The concentration of potassium bromide was 4 times that of Developer A.)

In addition, the fix solution has the same composition as that in Example 1.

TABLE 1

| Sample | Compound | Amount (mol/mol Ag) | Fog 31° C. | Fog 35° C. | Fog 37° C. | Relative Sensitivity 31° C. | Relative Sensitivity 35° C. | Relative Sensitivity 37° C. | Sensitivity Difference 37° C. − 31° C. | Gamma 31° C. | Gamma 35° C. | Gamma 37° C. | Gamma Difference 37° C. − 31° C. |
| --- | --- | --- | --- | --- | --- | --- | --- | --- | --- | --- | --- | --- | --- |
| 1 Control | — | — | 0.12 | 0.15 | 0.19 | 49 | 100 | 145 | 96 | 1.55 | 2.22 | 2.63 | 1.08 |
| 2 | Nitron* | $3.4 \times 10^{-4}$ | 0.12 | 0.14 | 0.17 | 50 | 91 | 126 | 76 | 1.60 | 2.03 | 2.45 | 0.85 |
| 3 | Nitron* | $6.8 \times 10^{-4}$ | 0.12 | 0.14 | 0.16 | 49 | 81 | 105 | 56 | 1.60 | 1.88 | 2.08 | 0.48 |
| 4 | Compound 6 | $3.4 \times 10^{-4}$ | 0.12 | 0.13 | 0.14 | 55 | 85 | 102 | 47 | 1.58 | 1.81 | 1.81 | 0.23 |
| 5 | Compound 9 | $1.7 \times 10^{-4}$ | 0.12 | 0.13 | 0.14 | 51 | 83 | 102 | 51 | 1.50 | 1.73 | 1.86 | 0.36 |
| 6 | Compound 13 | $1.7 \times 10^{-4}$ | 0.12 | 0.13 | 0.14 | 50 | 80 | 100 | 50 | 1.55 | 1.82 | 1.90 | 0.35 |
| 7 | Compound 7 | $0.9 \times 10^{-4}$ | 0.12 | 0.13 | 0.14 | 55 | 90 | 110 | 55 | 1.56 | 1.81 | 1.92 | 0.36 |
| 8 | Compound 15 | $0.9 \times 10^{-4}$ | 0.12 | 0.13 | 0.14 | 52 | 80 | 99 | 47 | 1.60 | 1.71 | 1.95 | 0.35 |
| 9 | Compound 23 | $0.5 \times 10^{-4}$ | 0.12 | 0.13 | 0.14 | 50 | 79 | 101 | 51 | 1.75 | 1.89 | 2.01 | 0.26 |

*Comparison Compound

In addition, the sensitivity shown in Table 1 is reciprocal of the exposure amount required to obtain a density of "fog + 1.0" and was shown as the relative value when the sensitivity of the control sample developed at 35° C. was defined as 100.

Also, the value of gamma was measured from a line passing through the point on the characteristic curve at a density obtained by adding 0.2 to the value of fog and the point at a density obtained by further adding 0.8 to the aforesaid density.

In addition, the value of fog is the value including the density of the base.

As is clear from the results shown in Table 1, seen that in Samples 4 to 9 using the compounds this invention, i.e., the mesoionic 1,2,4-triazolium-3-thiolate compounds, the formation of fog is effectively restrained as

| Processing Step | Temperature | Time |
| --- | --- | --- |
| 1. Development | 35° C. | 25 sec |
| 2. Fix | 35° C. | 25 sec |
| 3. Wash | 20° C. | 2 min |
| 4. Drying | 55° C. | 10 min |

After processing, the photographic properties were measured and the results thus obtained are shown in Table 2.

In addition, the sensitivity in Table 2 is the reciprocal of the exposure amount required to obtain a density of fog + 0.2 and was shown by the relative value when the sensitivity of Sample 1 developed at 35° C. was defined as 100.

TABLE 2

| Sample | Compound | Amount (mol/mol Ag) | Fog (A) | Fog (B) | Relative Sensitivity (A) | Relative Sensitivity (B) | Sensitivity Difference (B) − (A) | Gamma (A) | Gamma (B) | Gamma Difference (B) − (A) |
|---|---|---|---|---|---|---|---|---|---|---|
| 1 Control | — | — | 0.12 | 0.15 | 100 | 132 | 32 | 2.28 | 1.90 | −0.38 |
| 2 | Nitron* | $3.4 \times 10^{-4}$ | 0.12 | 0.14 | 95 | 129 | 34 | 2.10 | 1.86 | −0.24 |
| 3 | Nitron* | $6.8 \times 10^{-4}$ | 0.12 | 0.14 | 90 | 117 | 27 | 1.90 | 1.81 | −0.09 |
| 4 | Compound 6 | $3.4 \times 10^{-4}$ | 0.12 | 0.12 | 95 | 97 | 2 | 1.80 | 1.82 | 0.02 |
| 5 | Compound 9 | $1.7 \times 10^{-4}$ | 0.12 | 0.12 | 95 | 98 | 3 | 1.83 | 1.81 | −0.02 |
| 6 | Compound 13 | $1.7 \times 10^{-4}$ | 0.12 | 0.12 | 90 | 91 | 1 | 1.85 | 1.86 | 0.01 |
| 7 | Compound 7 | $0.9 \times 10^{-4}$ | 0.12 | 0.12 | 95 | 105 | 10 | 1.90 | 2.02 | 0.12 |
| 8 | Compound 15 | $0.9 \times 10^{-4}$ | 0.12 | 0.12 | 95 | 100 | 5 | 1.92 | 2.01 | 0.09 |
| 9 | Compound 23 | $0.5 \times 10^{-4}$ | 0.12 | 0.12 | 90 | 92 | 2 | 1.86 | 1.92 | 0.06 |

*Comparison Compound

As is clear from the results shown in Table 2, it can be seen that the Samples 4 to 9 using the compounds of this invention, i.e., the mesoionic 1,2,4-triazolium-3-thiolate compounds show very less change of photographic properties between the case of using Developer A and the case of using Developer B as compared to the Samples 2 and 3 using the comparison compound. In other words, the foregoing compounds used in this invention effectively restrain the increase of fog and sensitivity and the reduction of gamma in the development by the developer having the high concentration of potassium bromide. Usually, it is known that when a large amount of photographic materials are processed, the concentration of potassium bromide in the developer is increased but as shown in the above results, the compounds of this invention prevent the occurrence of deviation of photographic properties by the increase of the concentration of potassium bromide. This also shows that the foregoing compounds of this invention always give stable photographic properties even when a developer is fatigued.

EXAMPLE 3

Each of the Samples 1 to 9 as in Example 1 was exposed by the same manner as in Example 1 and subjected to the following processing using Developer C having the composition shown below.

| Processing Step | Temperature | Time |
|---|---|---|
| 1. Development | 20° C. | 4 min |
| 2. Fix | 20° C. | 4 min |
| 3. Wash | 20° C. | 2 min |
| 4. Drying | 55° C. | 10 min |

The processing compositions used for the above processing steps were as follows.

| Developer C | |
|---|---|
| Ethylenediaminetetraacetic Acid | 0.5 g |
| Sodium Sulfite (anhydrous) | 40.0 g |
| Sodium Hydroxide | 5.0 g |
| Hydroquinone | 20.0 g |
| 1-Phenyl-3-pyrazolidone | 0.8 g |
| Sodium Carbonate | 15.0 g |
| Glacial Acetic Acid | 2.5 g |
| Triethylene Glycol | 25.0 g |
| Potassium Bromide | 5.5 g |
| Water to make | 1 liter |

The pH of the composition was adjusted to about 10.20 at 25° C.
Fix Solution: Same as the fix solution in Example 1.

After processing, the photographic properties of each sample were measured and the results thus obtained are shown in Table 3.

As is clear from the results shown in the Table below, it can be seen that the samples using the comparison compound show reduced sensitivity at such a low temperature development, while Samples 4 to 9 using the compositions of this invention, the mesoionic 1,2,4-triazolium-3-thiolate compounds show increased sensitivity without accompanied by much increase of fog. This shows that the compounds of this invention give excellent photographic properties even at a low temperature processing of 20° C.

TABLE 3

| Sample | Compound | Amount (mol/mol Ag) | Fog | Relative Sensitivity | Gamma |
|---|---|---|---|---|---|
| 1 Control | — | — | 0.11 | 100 | 1.86 |
| 2 | Nitron* | $3.4 \times 10^{-4}$ | 0.11 | 98 | 1.81 |
| 3 | Nitron* | $6.8 \times 10^{-4}$ | 0.11 | 95 | 1.73 |
| 4 | Compound 6 | $3.4 \times 10^{-4}$ | 0.12 | 132 | 1.90 |
| 5 | Compound 9 | $1.7 \times 10^{-4}$ | 0.12 | 130 | 1.88 |
| 6 | Compound 13 | $1.7 \times 10^{-4}$ | 0.12 | 129 | 1.90 |
| 7 | Compound 7 | $0.9 \times 10^{-4}$ | 0.12 | 120 | 1.85 |
| 8 | Compound 15 | $0.9 \times 10^{-4}$ | 0.12 | 135 | 1.92 |
| 9 | Compound 23 | $0.5 \times 10^{-4}$ | 0.12 | 115 | 1.87 |

*Comparison Compound

While the invention has been described in detail and with reference to specific embodiments thereof, it will be apparent to one skilled in the art that various changes and modifications can be made therein without departing from the spirit and scope thereof.

What is claimed is:

1. A silver halide photographic material which is subjected to liquid development comprising a support having thereon at least one hydrophilic colloid layer containing at least one mesoionic 1,2,4-triazolium-3-thiolate compound in an amount from $1 \times 10^{-8}$ to $7 \times 10^{-3}$ moles per mole of silver in the photographic material.

2. A silver halide photographic material as in claim 1, wherein the mesoinoic 1,2,4-triazolium-3-thiolate compound is a compound represented by formula (I)

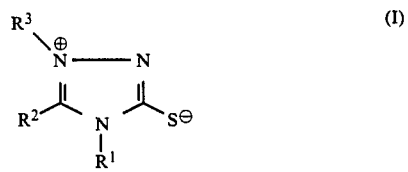

(I)

wherein $R^1$ represents a hydroxy group, a substituted or unsubstituted alkyl group having from 1 to 30 carbon atoms, a substituted or unsubstituted alkenyl group having from 3 to 30 carbon atoms, a substituted or unsubstituted cycloalkyl group having from 3 to 30 carbon atoms, a substituted or unsubstituted aryl group having from 6 to 30 carbon atoms, a substituted or unsubstituted heterocyclic ring having from 1 to 30 carbon atoms, —$NR^4R^5$ (wherein $R^4$ and $R^5$ each represents a hydrogen atom, a substituted or unsubstituted alkyl group having from 1 to 30 carbon atoms, a substituted or unsubstituted acyl group having from 2 to 30 carbon atoms, or a substituted or unsubstituted aryl group having from 6 to 30 carbon atoms; or said $R^4$ and $R^5$ combine with each other to form a ring), a substituted or unsubstituted acyloxy group having from 2 to 30 carbon atoms, or a substituted or unsubstituted alkoxy group having from 1 to 30 carbon atoms; $R^2$ represents a hydrogen atom, a substituted or unsubstituted alkyl group having from 1 to 30 carbon atoms, a substituted or unsubstituted cycloalkyl group having from 3 to 30 carbon atoms, a substituted or unsubstituted aryl group having from 6 to 30 carbon atoms, or a substituted or unsubstituted heterocyclic ring having from 1 to 30 carbon atoms; and $R^3$ represents a substituted or unsubstituted alkyl group having from 1 to 30 carbon atoms, a substituted or unsubstituted alkenyl group having from 1 to 30 carbon atoms, a substituted or unsubstituted cycloalkyl group having from 3 to 30 carbon atoms, a substituted or unsubstituted aryl group having from 6 to 30 carbon atoms, or a substituted or unsubstituted heterocyclic ring having from 1 to 30 carbon atoms; or $R^1$ and $R_2$, or $R_2$ and $R^3$ combine with each other to form a 5-, 6- or 7-membered heterocyclic ring.

3. A silver halide photographic material as in claim 1, wherein said substituted alkyl group, alkenyl group, cycloalkyl group, acyl group, acyloxy group, and alkoxy group represented by $R^1$, $R^2$, $R^3$, $R^4$ or $R^5$ has at least one substituent selected from the group consisting of an alkoxy group having from 1 to 7 carbon atoms, an alkoxycarbonyl group having from 2 to 7 carbon atoms, an alkoxy carbonylalkyl group having from 3 to 7 carbon atoms, a cyano group, a carboxy group, a hydroxy group, an amino group, and a sulfamoyl group.

4. A silver halide photographic material as in claim 1, wherein said substituted aryl group or heterocyclic group represented by $R^1$, $R^2$, $R^3$, $R^4$, or $R^5$ has at least one substituent selected from the group consisting of an alkoxy group having from 1 to 7 carbon atoms, an alkoxycarbonyl group having from 2 to 7 carbon atoms, an alkoxycarbonylalkyl group having from 3 to 7 carbon atoms, a cyano group, a carboxy group, a hydroxy group, an amion group, a sulfamonyl group, a halogen atom, and an acylamide group having 2–24 carbon atoms.

5. A silver halide photographic material as in claim 1, wherein said mesoionic 1,2,4-triazolium-3-thiolate compound is selected from the group consisting of the following compounds:

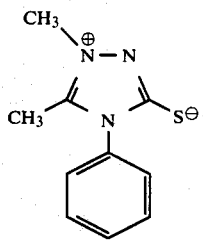

1

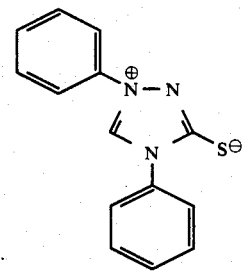

2

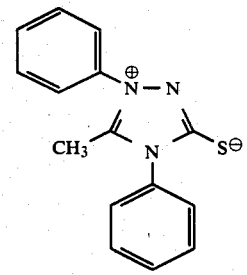

3

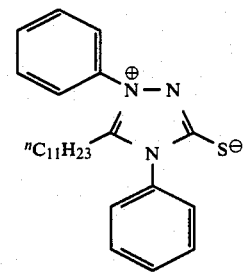

4

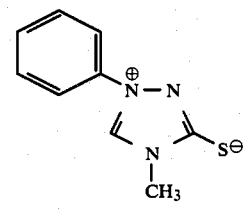

5

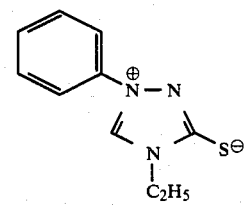

6

Compounds 7-20 (continued)

Chemical structures of triazolium-thiolate compounds numbered 7 through 20, each featuring a 1,2,4-triazole ring with N⁺ and S⁻ charges and various substituents (phenyl, alkyl, methoxyphenyl, chlorophenyl, etc.).

-continued
21
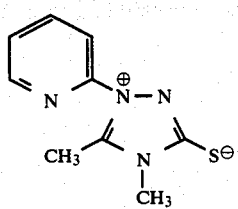
22
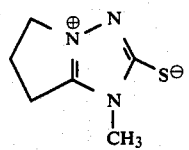
23
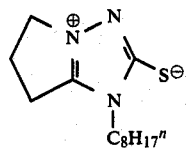
24
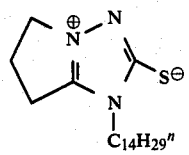
25
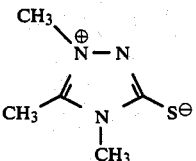
26
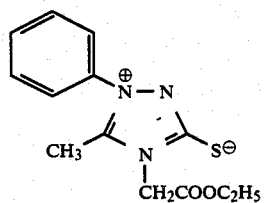
27
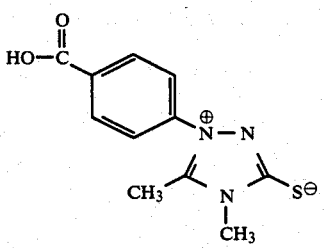
28
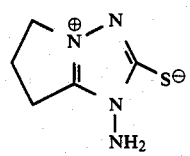
-continued
29
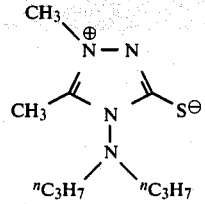
30
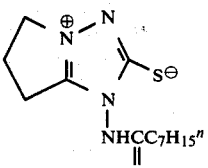
31
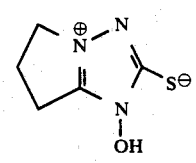
32
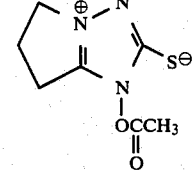
33
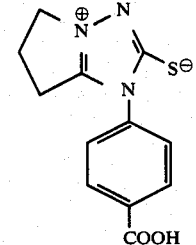
34
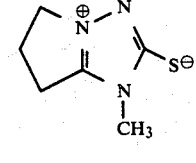
35
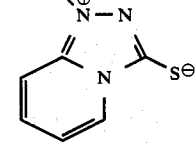
36
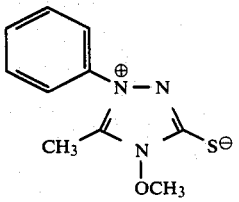

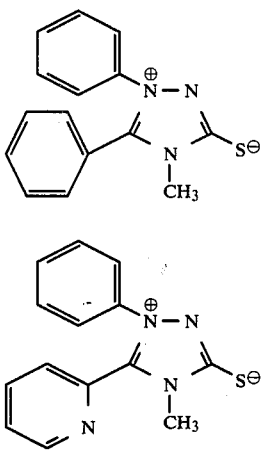

6. A silver halide photographic material as in claim 1, wherein said hydrophilic colloid layer is selected from the group consisting of a silver halide emulsion layer, a subbing layer, a protective layer, an interlayer, a filter layer, and an antihalation layer.

7. A silver halide photographic material as in claim 1, wherein said hydrophilic colloid layer is a silver halide emulsion layer.

8. A silver halide photographic material as claimed in claim 2,
    wherein (i):
    (1) when $R^1$ represents the hydroxy group, the heterocyclic ring, the $-NR^4R^5$ wherein $R^4$ and $R^5$ represents the acyl group or combined to form the ring, the acyloxy group or the alkoxy group, $R^2$ and $R^3$ each represents a group defined in claim 2;
    (2) when $R^2$ represents the hydrogen atom, the cycloalkyl group or the heterocyclic group, $R^1$ and $R^3$ each represents a group as described in claim 2;
    (3) when $R^3$ represents the alkenyl group or the heterocyclic ring, $R^1$ and $R^2$ represent one of the group defined in claim 2; or
    (ii) $R^1$ and $R^2$ or $R^2$ and $R^3$ combine with each other to form the 5-, 6- or 7-membered heterocyclic ring.

9. A method for forming an image comprising imagewise exposing and developing with a liquid developer a silver halide photographic material comprising a support having thereon at least one hydrophilic colloid layer containing at least one mesoionic 1,2,4-triazolium-3-thiolate compound in an amount from $1 \times 10^{-8}$ to $7 \times 10^{-3}$ moles per mole of silver in the photographic material.

10. A method as claimed in claim 9, wherein development is conducted at a temperature of 18° C. to 50° C.

11. A method as claimed in claim 10, wherein development is conducted at a temperature in the range 30° C. to 50° C.

12. The method of claim 9, wherein said mesoionic 1, 2, 4-triazolium-3-thiolate is contained in an amount of not less than $1 \times 10^{-5}$ mole per mole of silver in the silver halide photographic material.

13. A method as claimed in claim 9, wherein said mesoionic 1,2,4-triazolium-3-thiolate is contained in an amount of not less than $5 \times 10^{-5}$ to mole per mole of silver in the silver halide photographic material.

14. A silver halide photographic material as in claim 2, wherein $R^1$ represents the hydroxy group, the heterocyclic ring, the $-NR^4R^5$ (wherein $R^4$ and $R^5$ each represents the acyl group, or $R^4$ and $R^5$ combine with each other to form a ring), the acyloxy group, the alkoxy group, $R^2$ represents the hydrogen atom, the cycloalkyl group, the heterocyclic ring, $R^3$ represents the alkenyl group, the heterocyclic ring, or $R^1$ and $R^2$, or $R^2$ and $R^3$ combine with each other to form the 5-, 6- or 7-membered heterocyclic ring.

15. A silver halide photographic material as claimed in claim 1, wherein said mesoionic 4-triazolium-3-thiolate is contained in an amount of not less than $1 \times 10^{-5}$ mole per mole of silver in the silver halide photographic material.

16. A silver halide photographic material as claimed in claim 1, wherein said mesoionic 4-triazolium-3-thiolate is contained in an amount of not less than $5 \times 10^{-5}$ mole per mole of silver in the silver halide photographic material.

17. A method as claimed in claim 9, wherein the mesoionic 1,2,4-triazolium-3-thiolate compound is a compound represented by formula (I)

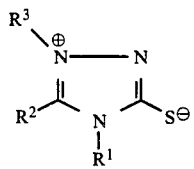

wherein $R^1$ represents a hydroxy group, a substituted or unsubstituted alkyl group having from 1 to 30 carbon atoms, a substituted or unsubstituted alkenyl group having from 3 to 30 carbon atoms, a substituted or unsubstituted cycloalkyl group having from 3 to 30 carbon atoms, a substituted or unsubstituted aryl group having from 6 to 30 carbon atoms, a substituted or unsubstituted heterocyclic ring having from 1 to 30 carbon atoms, $-NR^4R^5$ (wherein $R^4$ and $R^5$ each represents a hydrogen atom, a substituted or unsubstituted alkyl group having from 1 to 30 carbon atoms, a substituted or unsubstituted acyl group having from 2 to 30 carbon atoms, or a substituted or unsubstituted aryl group having from 6 to 30 carbon atoms; or said $R^4$ and $R^5$ combine with each other to form a ring), a substituted or unsubstituted acyloxy group having from 2 to 30 carbon atoms, or a substituted or unsubstituted alkoxy group having from 1 to 30 carbon atoms; $R^2$ represents a hydrogen atom, a substituted or unsubstituted alkyl group having from 1 to 30 carbon atoms, a substituted or unsubstituted cycloalkyl group having from 3 to 30 carbon atoms, a substituted or unsubstituted aryl group having from 6 to 30 carbon atoms, or a substituted or unsubstituted heterocyclic ring having form 1 to 30 carbon atoms; and $R^3$ represents a substituted or unsubstituted alkyl group having from 1 to 30 carbon atoms, a substituted or unsubstituted alkenyl group having from 1 to 30 carbon atoms, a substituted or unsubstituted cycloalkyl group having from 3 to 30 carbon atoms, a substituted or unsubstituted aryl group having form 6 to 30 carbon atoms, or a substituted or unsubstituted heterocyclic ring having from 1 to 30 carbon atoms; or $R^1$ and $R^2$, or $R^2$ and $R^3$ combine with each other to form a 5-, 6- or 7-membered heterocyclic ring.

18. A method as claimed in claim 17,
    (1) when $R^1$ represents the hydroxy group, the heterocyclic ring, the $-NR^4R^5$ wherein $R^4$ and $R^5$ represents the acyl group or combine to form the ring, the acyloxy group or the alkoxy group $R^2$ and $R^3$ each represents a group defined in claim 2;
(2) when $R^2$ represents the hydrogen atom, the cycloalkyl group or the heterocyclic group $R^1$ and $R^3$ each represents a group as described in claim 2;
(3) when $R^3$ represents the alkenyl group or the heterocyclic ring, $R^1$ and $R^2$ each represent one of the groups defined in claim 2; or
(ii) $R^1$ and $R^2$ or $R^2$ and $R^3$ combine with each other to form the 5-, 6- or 7-membered heterocyclic ring.

19. A method as claimed in claim 17, wherein $R^1$ represents the hydroxy group, the heterocyclic ring, the —$NR^4R^5$ (wherein $R^4$ and $R^5$ each represents the acyl group or $R^4$ and $R^5$ combine with each other to form a ring), the acyloxy group, the alkoxy group, $R^2$ represents the hydrogen atom, the cycloalkyl group, the heterocyclic ring, $R^3$ represents the alkenyl group, the heterocyclic ring, or $R^1$ and $R^2$, or $R^2$ and $R^3$ combine with each other to form the 5-, 6- or 7-membered heterocyclic ring.

20. A method as claimed in claim 9, wherein said hydrophilic colloid layer is selected from the group consisting of a silver halide emulsion layer, a subbing layer, a protective layer, an interlayer, a filter layer, and an antihalation layer.

* * * * *